(12) United States Patent
Barak et al.

(10) Patent No.: US 10,702,299 B2
(45) Date of Patent: Jul. 7, 2020

(54) ATHERECTOMY DEVICE

(71) Applicant: Taryag Medical Ltd., Caesarea Industrial Park (North) (IL)

(72) Inventors: Swi Barak, Caesarea (IL); Aharon Cohen, Ramot Hashavim (IL)

(73) Assignee: Taryag Medical Ltd., Caesaria Industrial (IL)

( * ) Notice: Subject to any disclaimer, the term of this patent is extended or adjusted under 35 U.S.C. 154(b) by 136 days.

(21) Appl. No.: 15/323,410

(22) PCT Filed: Jul. 3, 2015

(86) PCT No.: PCT/IL2015/050690
§ 371 (c)(1),
(2) Date: Dec. 31, 2016

(87) PCT Pub. No.: WO2016/001932
PCT Pub. Date: Jan. 7, 2016

(65) Prior Publication Data
US 2017/0143372 A1   May 25, 2017

(30) Foreign Application Priority Data

Jul. 3, 2014  (IL) .......................................... 233519

(51) Int. Cl.
*A61B 17/3207* (2006.01)
*A61B 17/22* (2006.01)

(52) U.S. Cl.
CPC ................ *A61B 17/320725* (2013.01); *A61B 17/320758* (2013.01); *A61B 2017/22068* (2013.01);
(Continued)

(58) Field of Classification Search
CPC ........ A61B 17/3207; A61B 17/320725; A61B 17/320758; A61B 2017/320733; A61B 2017/320741; A61B 2017/320766
See application file for complete search history.

(56) References Cited

U.S. PATENT DOCUMENTS 5,490,859 A * 2/1996 Mische .......... A61B 17/320725
606/159
6,156,046 A * 12/2000 Passafaro ............. A61B 17/221
128/898
(Continued)

FOREIGN PATENT DOCUMENTS

CN    102223846 A    10/2011
JP    2011-522596    8/2011
(Continued)

OTHER PUBLICATIONS

Patent Cooperation Treaty, International Search Report, International Patent Application No. PCT/IL2015/050690, dated Oct. 26, 2015, 5 Pages.
(Continued)

*Primary Examiner* — Sarah A Simpson
(74) *Attorney, Agent, or Firm* — Fenwick & West LLP

(57) ABSTRACT

An atherectomy device comprising a rotatably motor-driven flexible hollow shaft that is coaxial with a longitudinal axis of the guidewire; an annular distal end of the hollow shaft having a diameter that is only slightly larger than the diameter of the guidewire and configured with cutting surfaces for piercing hardened atherosclerotic plaque! a tubular sleeve secured to a first peripheral surface of the hollow shaft and configured with cutting surfaces for enlarging an opening formed in the plaque; and an asymmetric cutting unit extending between the sleeve and a second peripheral surface of the hollow shaft, to enable eccentric rotation of the hollow shaft for cutting and removing addi-
(Continued)

tional occlusive material from the blood vessel to open a chronic total occlusion. In one embodiment, the cutting unit is a helical strand unit having a polygonal cross section with a first side that atraumatically contacts a blood vessel wall.

21 Claims, 9 Drawing Sheets

(52) U.S. Cl.
CPC ............... *A61B 2017/22082* (2013.01); *A61B 2017/22094* (2013.01); *A61B 2017/320733* (2013.01)

(56) References Cited

U.S. PATENT DOCUMENTS

| | | | |
|---|---|---|---|
| 6,818,002 | B2 | 11/2004 | Shiber |
| 2002/0007190 | A1 | 1/2002 | Wulfman et al. |
| 2003/0208215 | A1* | 11/2003 | Uflacker ........ A61B 17/320725 606/159 |
| 2008/0004643 | A1 | 1/2008 | To et al. |
| 2010/0274270 | A1 | 10/2010 | Patel et al. |
| 2012/0209273 | A1* | 8/2012 | Zaretzka .......... A61B 17/32002 606/80 |

FOREIGN PATENT DOCUMENTS

| | | |
|---|---|---|
| WO | WO 2005/120628 A2 | 12/2005 |
| WO | WO 2010/002507 A1 | 1/2010 |
| WO | WO 2012/050877 A1 | 4/2012 |
| WO | WO 2013/056262 A1 | 4/2013 |
| WO | WO 2014/106847 A1 | 7/2014 |

OTHER PUBLICATIONS

Patent Cooperation Treaty, Written Opinion of the International Searching Authority, International Patent Application No. PCT/IL2015/050690, dated Oct. 26, 2015, 5 Pages.

Patent Cooperation Treaty, International Preliminary Report on Patentability, International Patent Application No. PCT/IL2015/050690, dated Dec. 12, 2016, 18 Pages.

Extended European Search Report, European Patent Application No. 15814721.5, dated Mar. 21, 2018, 11 pages.

First Office Action, Chinese Patent Application No. 201580036472.5, dated Jul. 27, 2018, 9 pages.

Japanese Office Action, Japanese Patent Application No. 2016-575959, dated Mar. 19, 2019, 11 pages.

* cited by examiner

ATHERECTOMY DEVICE

FIELD OF THE INVENTION

The present invention relates to the field of rotational atherectomy devices for removing plaque and clots that have accumulated on a blood vessel wall. More particularly, the invention relates to an atherectomy device that is capable of opening a chronic total occlusion.

BACKGROUND OF THE INVENTION

Some rotational atherectomy devices for removing plaque and clots that have accumulated on a blood vessel wall are known from the prior art. Relatively soft, cholesterol-rich atheromatous material often hardens into a calcified atherosclerotic plaque to restrict the flow of blood.

Several methods are currently available to form a channel through a blocked blood vessel. Initially, a guidewire is used to probe a channel through the blockage in the blood vessel in order to reach a downstream unblocked blood vessel portion. After the guidewire has been advanced through the blockage, a physician manually guides a catheter through an introducer sheath and over the guidewire to the atheroma site. For example, an angioplasty balloon catheter is passed over the guidewire and is inflated to dilate the blockage.

This method is known to succeed in soft or partial blockages of a blood vessel, through which the guidewire can be easily passed. It carries the risk, however, of causing tears in the arterial wall due to the diameter of the inflated balloon. Moreover, such methods do not remove the atheromatous material from the vessel.

Other methods use catheter devices having a rotating or vibrating tip operated by an external drive unit or power source, which is coupled to the tip by a flexible drive element, such as a cable, spring or shaft. Such devices such as disclosed in U.S. Pat. No. 6,818,002 are introduced into a blood vessel over a guidewire, and the atheroma or blood clot material is shaved from the wall of the artery, while risking perforation of the arterial wall, and may then be aspirated by the catheter out of the vessel in order to prevent distal embolization.

Such methods employing a guidewire to first probe a channel through the blockage in the blood vessel and then introducing the rotating or vibrating device over the guidewire to remove the atheroma are in less use because most physicians can treat the occluded vessel with a balloon or stent if the guidewire has already passed the occluded segment.

WO 2013/056262 discloses a rotational atherectomy device having a handle, a distal cutter assembly for cutting and capturing occlusive material, and a catheter extending between the handle and the cutter assembly. A motor housed within the handle causes a torque shaft connected to the cutter assembly to rotate concentrically. The outer diameter of the cutter assembly is greater than or equal to that of the catheter to maximize the overall cutting area. The reduced diameter of the catheter body reduces frictional contact with the vessel wall and also permits the injection of radiographic contrast material around the catheter body in the guide sheath.

This atherectomy device configuration has some deficiencies. Due to its relatively large dimensions, the cutter assembly has difficulty in penetrating the blockage when contacting the smooth and hardened plaque, and often slides towards the vessel wall in response to the encountered resistance to the removal of the occlusive material. Even if the prior art atherectomy device were successful somehow in initially penetrating the hardened plaque, it would have difficulty in forming an opening in the plaque since the rotating cutter assembly follows a concentric path with respect to the guidewire, and therefore is able to cut only that occlusive material coinciding with, or adjoining, the guidewire; if the occlusive material adjoining the guidewire is hardened, however, it generally cannot be penetrated. Additionally, the physician is not able to accurately visualize the location of the distal cutter assembly by means of the contrast material since the contrast material is injected between the catheter and the introducer sheath at a distance from the distal end.

Copending International Publication WO 2014/106847 by the same Applicant discloses an expandable atherectomy device, comprising a rotatably motor-driven flexible hollow shaft that is slidable over a guidewire introducible through a flexible catheter tube and is coaxial with the longitudinal axis of the guidewire, an expandable cutting unit connected to a distal end of the hollow shaft, and an actuator which is operable to induce selective expansion of the cutting unit. The hollow shaft comprises inner and outer tubular portions, which may be embodied by inner and outer cables and which are simultaneously rotatable while one of the inner and outer tubular portions slides over the other in a direction substantially parallel to the longitudinal axis. The cutting unit is expandable in response to an actuated action which causes two separated ends of the cutting unit to be brought closer together. The cutting unit, when expanded, is eccentrically rotatable about the longitudinal axis to cut and remove atheromous material from a blood vessel.

Although this atherectomy device is very effective in removing atheromous material and in being selectively introducible to both large and small sized blood vessels, several mechanical difficulties have been found:

1. As result of the compression force applied to the hollow shaft that causes the two ends of the cutting unit to be brought closer together, the coils of the outer cable tend to expand and to be separated from each other. The outer diameter of the cable becomes enlarged, increasing the frictional force with a plastic tube into which removed atheromous material is drawn and shortening the total length of the hollow shaft.

2. Although the proximally located actuator allows relative linear movement and simultaneous rotation of the inner and outer tubular portions, the hollow shaft is not provided with a mechanism at its distal end to assure uniform rotation of the inner and the outer portions. Without such a mechanism, the cutting unit is subject to failure.

3. The angle of the cutting unit made by the coils of the external cable must be optimized to reduce force and fatigue at the bending points, and to assure maximum of flexibility and strength of these coils in close and open conditions. Moreover, if the external cable is made of memory metal (Nitinol) and the internal cable is made of stainless steel, it is extremely difficult to weld the two metal compositions together. More importantly, welding of Nitinol creates a local thermal effect that weakens the material and increase the possibility to break at the weld zone.

4. The physician generally needs to inject contrast material after the removal of atheroma from a blood vessel, to determine if the treated vessel is now unoccluded and to verify that no damage was made to the blood vessel wall. In order to do this, the atherectomy catheter must be removed, and replaced by another catheter to be introduced to the atheroma site over the guidewire. This requires time, especially if the atheroma is not fully removed and an additional operation with the atherectomy catheter is required.

It is an object of the present invention to provide a rotatable atherectomy device that is assured of penetrating hardened plaque within a blood vessel without risking perforation of the blood vessel wall.

It is an additional object of the present invention to provide a rotatable atherectomy device that is capable of cutting occlusive material which does not adjoin the guidewire over which the catheter is introduced into the blood vessel.

It is an additional object of the present invention to provide a rotatable atherectomy device that is not dependent upon a guidewire that first probes a channel through the blockage.

It is an additional object of the present invention to provide an atherectomy device that facilitates the accurate visualization of its distal end by means of contrast material, and without requiring separate catheters for an atheroma removing operation and for injection of contrast material.

It is yet an additional object of the present invention to provide, in one embodiment, an atherectomy device having an expandable cutting unit and a hollow shaft consisting of coaxial inner and outer cables arranged such that the coils of the outer cable will remain in abutting relation with each other and in a substantially uniform shape and diameter.

Other objects and advantages of the invention will become apparent as the description proceeds.

SUMMARY OF THE INVENTION

The present invention provides an atherectomy device for opening a chronic total occlusion within a blood vessel, comprising a rotatably motor-driven flexible hollow shaft that is slidable over a guidewire and is coaxial with a longitudinal axis of the guidewire; an annular distal end of the hollow shaft having a diameter that is only slightly larger than the diameter of the guidewire and configured with cutting surfaces for piercing hardened atherosclerotic plaque of a chronic total occlusion that has accumulated within a blood vessel; a tubular sleeve proximally spaced from said distal end of the hollow shaft, and fitted over, and secured to a first peripheral surface of the hollow shaft, wherein a distal end of said sleeve has a slightly larger diameter than said distal end of the hollow shaft and is configured with cutting surfaces for enlarging an opening formed in the plaque; and an asymmetric cutting unit extending between said sleeve and a second peripheral surface of the hollow shaft which is proximally spaced from said first peripheral surface, to enable eccentric rotation of the hollow shaft about the longitudinal axis for cutting and removing additional occlusive material from the blood vessel to open the chronic total occlusion.

In one aspect, the asymmetric cutting unit is a helical strand unit that radially protrudes from the sleeve and from the second peripheral surface of the hollow shaft, said helical strand unit being wound about the hollow shaft in such a way that only one diametrical end of the hollow shaft is surrounded by said helical strand unit for a given axial length of the hollow shaft.

In one aspect, the helical strand unit has a polygonal cross section that is configured with a first side adapted to atraumatically contact a wall of the blood vessel and with a sharp edge, suitable for cutting the occlusive material, at a vertex of said first side and of an adjacent second side.

In one aspect, the asymmetric cutting unit is connected or secured to the sleeve and to a second peripheral surface of the hollow shaft.

In one aspect, the hollow shaft comprises coaxial inner and outer tube layers to each of which a corresponding end of the helical strand unit is secured or attached, and an actuator which is operable to cause longitudinal displacement of one of said inner and outer tube layers relative to the other and to induce selective expansion of the helical strand unit.

In one aspect, the actuator is configured with a proximal port in communication with a lumen of the hollow shaft, through which contrast material is injectable.

In one aspect, the outer tube layer is a cable of multi-coil construction.

In one aspect, the atherectomy device further comprises a coil expansion limiter secured or attached to the outer tube layer, for increasing compressive strength of the outer tube layer. The coil expansion limiter may be a helical mono-coil spring wound over the cable of the outer tube layer and having a larger pitch than the pitch of the coils of the outer tube layer, to maintain a substantially uniform outer cable shape and diameter. A pitch ratio of the outer cable to the mono-coil spring may range from 1.0-1.1 to 1.0-10.

In one aspect, the atherectomy device further comprises an additional tubular sleeve fitted over, and secured to the outer cable at the second peripheral surface of the hollow shaft, a first aperture being formed in said additional sleeve by which a portion of the helical strand unit is fixated and a second aperture for receiving a corresponding end of the mono-coil spring being formed in said additional sleeve.

In one aspect, the sleeve is connected to the outer tube layer, for ensuring coaxial and concurrent rotation of the inner and outer tube layers substantially throughout the entire length of the hollow shaft.

In one aspect, the atherectomy device further comprises a metal tube surrounding and engaged with the sleeve, wherein a distal end of the helical strand unit is secured said metal tube and said sleeve. A distal end of the metal tube may be formed with one or more cutting surfaces for further enlarging the opening formed in the plaque.

The present invention is also directed to a cutting unit for use in removing occlusive material within a blood vessel, comprising a helical strand unit wound about a shaft of an atherectomy device in such a way that only one diametrical end of the shaft is surrounded by said helical strand unit for a given axial length of the shaft to enable eccentric rotation of the shaft about its longitudinal axis for cutting and removing occlusive material from the blood vessel, wherein said helical strand unit has a polygonal cross section that is configured with a first side adapted to atraumatically contact a wall of the blood vessel and with a sharp edge, suitable for cutting the occlusive material, at a vertex of said first side and of an adjacent second side.

DETAILED DESCRIPTION OF PREFERRED EMBODIMENTS

The atherectomy device of the present invention comprises a motor-driven and flexible hollow shaft that is slidable over a guidewire. While the distal end of prior art rotatable atherectomy devices for removing occlusive material from a blood vessel has a relatively large and uniform diameter and tends to slip towards the blood vessel wall following contact with hardened plaque, often perforating the wall, the rotatable atherectomy device of the present invention has a distal end with a varying diameter that gradually increases from a small diameter suitable to pierce the hardened plaque to an increased diameter suitable to enlarge the pierced opening.

The unique configuration of the atherectomy device facilitates opening of a chronic total occlusion (CTO) that is not penetrable by a guidewire, although it is also suitable for cutting and removing other occlusive material as well. Prior art atherectomy devices are incapable of reliably opening a CTO due to the prolonged blockage that results in severely hardened plaque. Patients suffering from a CTO have had to be treated heretofore with a peripheral bypass or with a leg amputation. The minimally invasive approach (also known as endovascular) using the atherectomy device of the present invention therefore helps patients from avoid avoiding much pain and suffering.

Figure 1:
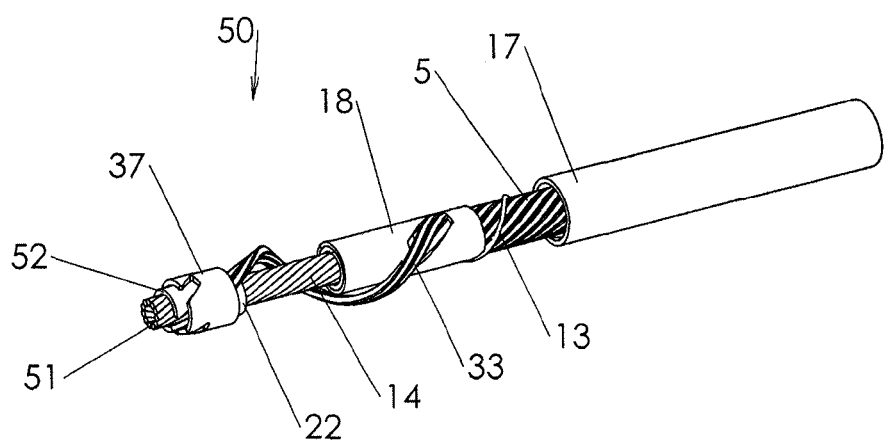
FIG. 1 is a perspective view of an atherectomy device, according to one embodiment of the present invention, shown in a collapsed condition.

FIG. 1 illustrates a perspective view of a distal portion of a rotatable atherectomy device, generally designated by numeral 50, according to one embodiment of the present invention. Atherectomy device 50 comprises a flexible rotatable hollow shaft 13 received within the interior of plastic tube 17 into which removed occlusive material is drawn by means of an aspiration system. Hollow shaft 13 comprises outer tubular portion 5 and inner tubular portion 14 that are able to rotate simultaneously while sliding one over the other in a direction parallel to the longitudinal axis of the shaft.

An expandable helical cutting unit 33 extends between tubular sleeves 18 and 22, which are fitted over, and secured such as by laser welding to, outer tubular portion 5 and inner tubular portion 14, respectively. The use of a helical cutting unit is advantageous in that it promotes good penetrability into hardened plaque, similarly to the operation of a screw or drill bit, but with significant material savings. Helical cutting unit 33 is wound about hollow shaft 13 by a sufficiently long pitch such that only one diametrical end of the hollow shaft is partially surrounded by helical cutting unit 33 for a given axial length of the hollow shaft. The long pitch is suitable for the fast rotational speeds of hollow shaft 13 that are characteristic of occlusive material removal operations, e.g. 5000 rpm or greater. This asymmetrical configuration of helical cutting unit 33 results in the eccentric rotation of hollow shaft 13, contributing to clinical advantages, as will be described hereinafter.

An adjusting member 9 (FIG. 6) is provided for selectively expanding cutting unit 33 away from the longitudinal axis of hollow shaft 13, typically by controlled retraction of the inner tubular portion 14 by sliding movement inside outer tubular portion 5. Retraction of the inner tubular portion brings the ends of the flexible cutting unit together, thus causing the cutting unit to expand outwardly away from the longitudinal axis of the shaft and enlarging the area encompassed by the flexible cutting unit. The expanded cutting unit facilitates disintegration and removal of the atheroma from the blood vessel when rotating.

Figure 6:
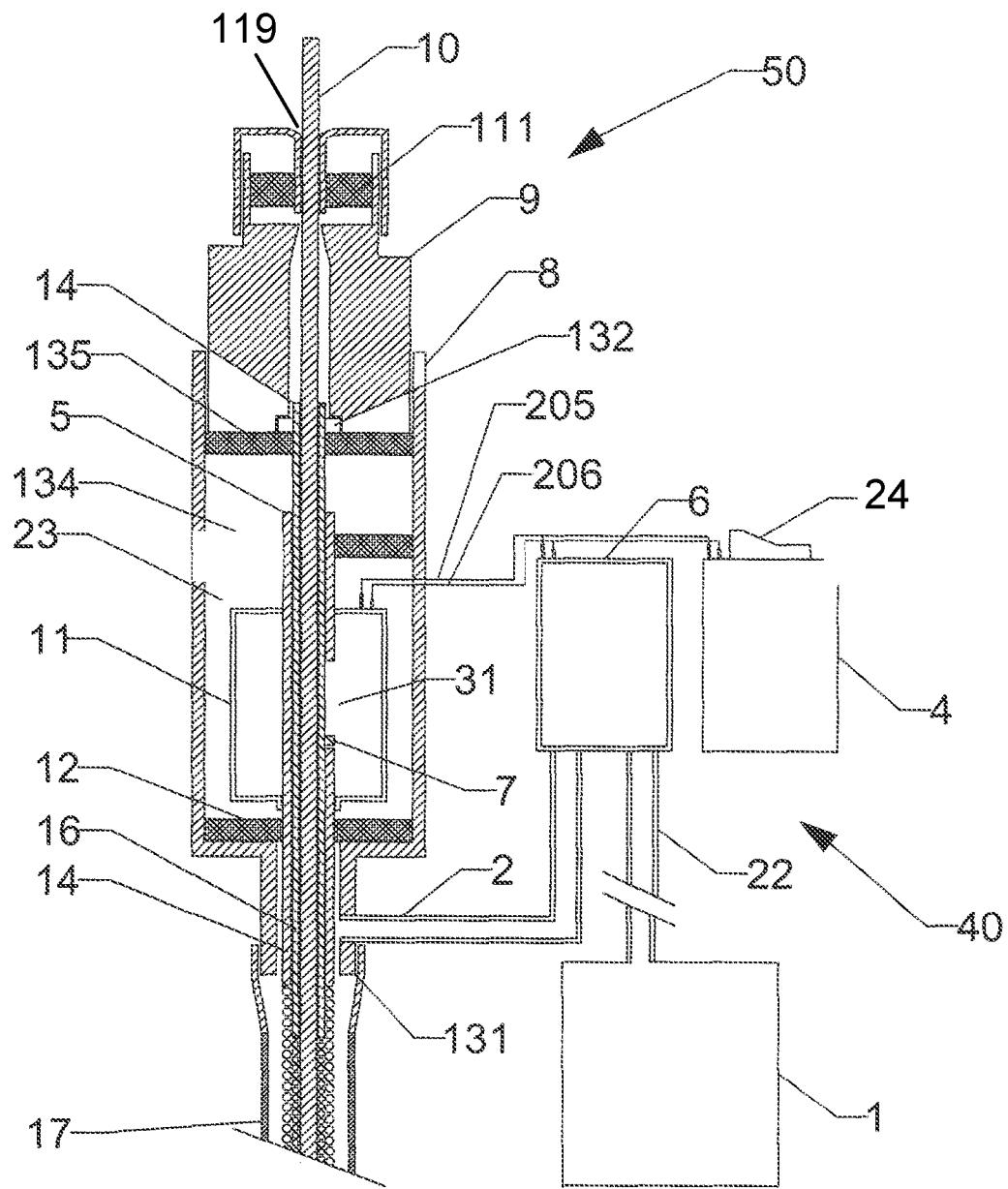
FIGS. 6 and 7 are a partial longitudinal cross section of the atherectomy device of FIG. 1, showing a proximal portion thereof including an aspiration system and an actuator in two different positions, respectively.

As shown in FIG. 6, guidewire 10 is received within the interior of inner tubular portion 14. The proximal end of plastic tube 17 is connected to a distal portion of handle body 8, within which is housed a motor 11 for driving hollow shaft 13. A physician uses handle body 8 to manipulate the atherectomy device during the course of a material removal operation.

Inner tubular portion 14 distally protrudes from outer tubular portion 5. The distal end of inner tubular portion 14, which has a diameter only slightly greatly than the guidewire for guiding atherectomy device 50 through a blood vessel, e.g. ranging from 0.1-0.6 mm, and which first encounters the occlusive material, is formed with circumferentially extending cutting teeth 51, or any other type of cutting surfaces, for example by a micro-laser cutting technique.

Sleeve 22 slightly proximally spaced from distal cutting teeth 51 is fitted over, and secured to outer tubular portion 5. The distal end of sleeve 22 is formed with circumferentially extending cutting teeth 52, or any other type of cutting surfaces, constituting means for increasing an opening formed in the hardened plaque. Since sleeve 22 protrudes radially from outer tubular portion 5, cutting teeth 52 have a slightly larger diameter than cutting teeth 51, a difference on the order of only tenths of a millimeter.

Figure 3:
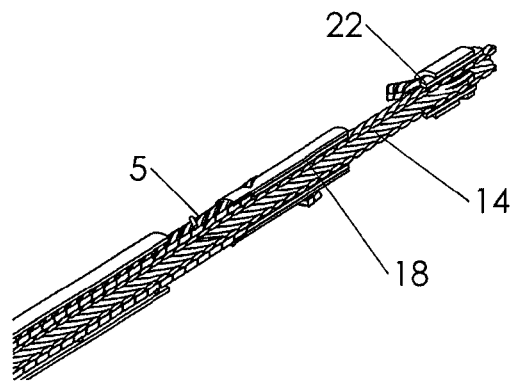
FIG. 3 is a perspective, cross sectional view of a tubular sleeve used in conjunction with the atherectomy device of FIG. 1.

As shown in FIG. 3, sleeve 18 is connected to the distal end of outer tubular portion 5, to provide a reactive force when the expandable cutting unit undergoes extreme resistance due to hard atheroma, for example when attempting to drill a chronic total occlusion.

A third means for penetrating and removing occlusive material is in the form of sharpened metal tube 37, which may be fitted over locking device 22, and therefore of a slightly larger diameter than sleeve 22, a difference on the order of only tenths of a millimeter.

Figure 4:
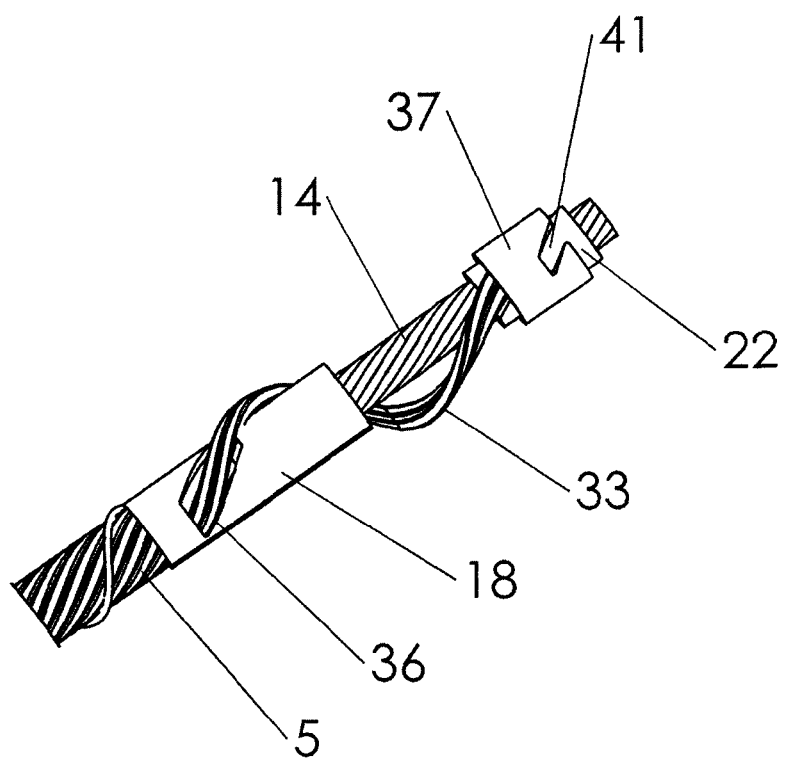
FIG. 4 is a perspective view of a cutting unit fixation device.
Figure 5:
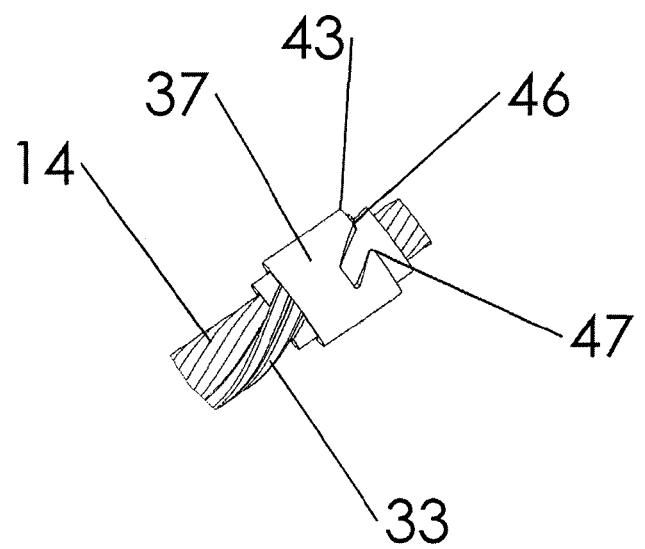
FIG. 5 is an enlargement of the fixation device of FIG. 4.

As shown in FIGS. 4 and 5, tube 37 is configured with one or more slots 41 that extend proximally from the distal edge 43 of the tube. Each of the slots 41 is formed obliquely with respect to distal edge 43, forming cutting surfaces 46 and 47 at the two lateral ends of slot 41, respectively, by which the atherectomy device is able to penetrate a proximal surface of hard atheroma material. Helical cutting unit 33 in the collapsed condition radially protruding a distance that defines a slightly larger diameter than tube 37, a difference on the order of only tenths of a millimeter, is then able to remove additional atheroma material.

Figure 2:
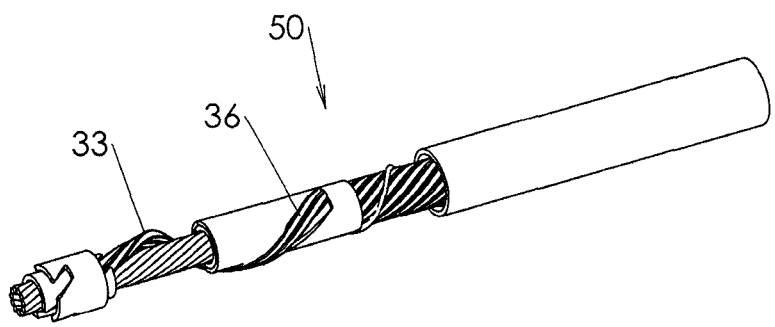
FIG. 2 is a perspective view of the atherectomy device of FIG. 1, shown in an expanded condition.

FIG. 2 illustrates atherectomy device 50 when cutting unit 33 is set to an expanded condition, such that the defined diameter increases on the order of several millimeters.

The four cutting means provided with atherectomy device 50 thus define cutting surfaces of gradually increased size to allow the pierced opening to be suitably enlarged.

FIG. 6 illustrates a proximal portion of atherectomy device 50, which is generally disposed externally to a patient's body.

Plastic tube 17 is connected to the distal tip of handle body 8 by schematically illustrated connection means 131, which may be a flexible shaft connector, a regular Luer lock type connector, or any other suitable connector. Connection means 131 may be detachable.

The aspiration system 40 comprises a miniature vacuum pump 6 and a collection bag 1, to which are drawn the disintegrated atheroma particles via first aspiration line 2 extending from the annular space between the distal narrowed tip of catheter body 8 and outer tubular portion 14 to vacuum pump 6, and second aspiration line 22 extending from vacuum pump 6 to collection bag 1. Battery unit 4 having a switch 24 powers both vacuum pump 6 and motor 11.

Motor 11 connected to battery unit 4 by wires 205 and 206 is housed within chamber 23 of handle body 8 between distal seal 12 and intermediate seal 134, which are fixed and through which tubular portions 5 and 14 of the hollow coaxial shaft pass. Motor 11, which is sealed by fixed seals 12 and 134 and by displaceable seal 135, is drivingly engaged with outer tubular portion 5. Heat shrink material, e.g. adhesive material, may be advantageously used to engage motor 11 with outer tubular portion 5 even though the latter may be made from Nitinol.

A longitudinally displaceable adjusting member 9 for initiating selective expansion of the flexible cutting unit is fitted within handle body 8. A seal 135 connected to the distal face of adjusting member 9 is sealingly engaged with the inner wall of catheter body 8. The proximal end of inner tubular portion 14 is connected by adhesion or laser welding to rotating bearing 132, which is seated in a complementary cavity formed in adjusting member 9 and in contact with the proximal face of seal 135. This arrangement allows inner tubular portion 14 to be longitudinally displaced together with adjusting member 9 in or out of handle body 8 while simultaneously rotating.

Inner tubular layer 14 is longitudinally displaceable since it is connected to rotating bearing 132. Distal displacement of adjusting member 9 reduces the spacing between sleeves 18 and 22 and causes the helical cutting unit to expand, as shown in FIG. 2. Conversely when adjusting member 9 is proximally displaced, sleeves 18 and 22 are caused to be separated, so that the expanded cutting unit is forced to collapse, as shown in FIG. 1.

Figure 7:
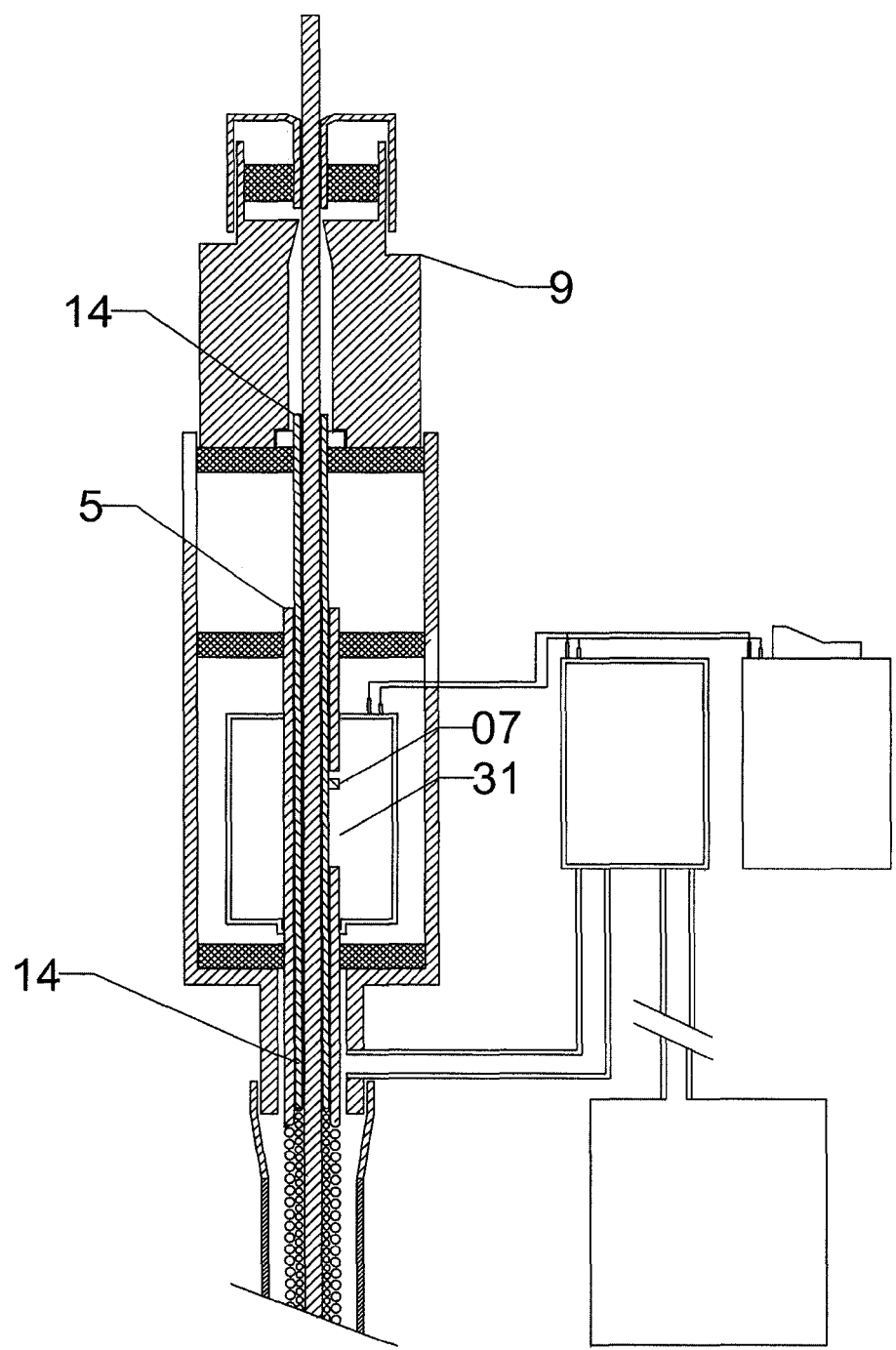

To limit the longitudinal displacement of adjusting member 9, outer tubular portion 5 is formed with a long and narrow window 31 that may be positioned within the confines of motor chamber 23. Within the interior of window 31 a pin 7 welded or otherwise attached to inner tubular portion 14 is allowed to change its position without interference while adjusting member 9 is being longitudinal displaced. However, when pin 7 contacts one of the lower and upper edges of window 31, as shown in FIGS. 6 and 7, respectively, at a corresponding extreme position of adjusting member 9 and of inner tubular portion 14 connected thereto, additional longitudinal displacement in a same direction is prevented. Nevertheless pin 7 enables outer tubular portion 5 and inner tubular portion 14 to rotate in unison.

It will be appreciated that any other suitable adjusting member, actuator or aspiration system is also within the scope of the invention.

Contrast material for accurately locating the position of the atherectomy device distal tip, or verifying that a blood vessel is unoccluded and its wall is not damaged following an occlusive material removing operation, is injectable through the lumen of inner tubular portion 14 via central opening 119. By injecting the contrast material through the annular space of opening 119 surrounding guidewire 10, the same catheter may be advantageously used for both an occlusive material removing operation and injection of the contrast material, as opposed to prior art methods for which two separate catheters are needed. Inner tubular portion 14 may be covered with thin-walled and liquid impervious heat shrink material, thereby transforming the hollow shaft to a sealed tube through which the injected contrast material can reliably flow to the occlusion site. Alternatively, a sealant such as parylene, polyamide, polymeric material and sprayed plastic material can be applied to the inner surface of a multi-coiled inner tubular portion. If so desired, the entire inner tubular portion 14 may be made of a liquid impervious, molded or extruded plastic material.

Figure 12:
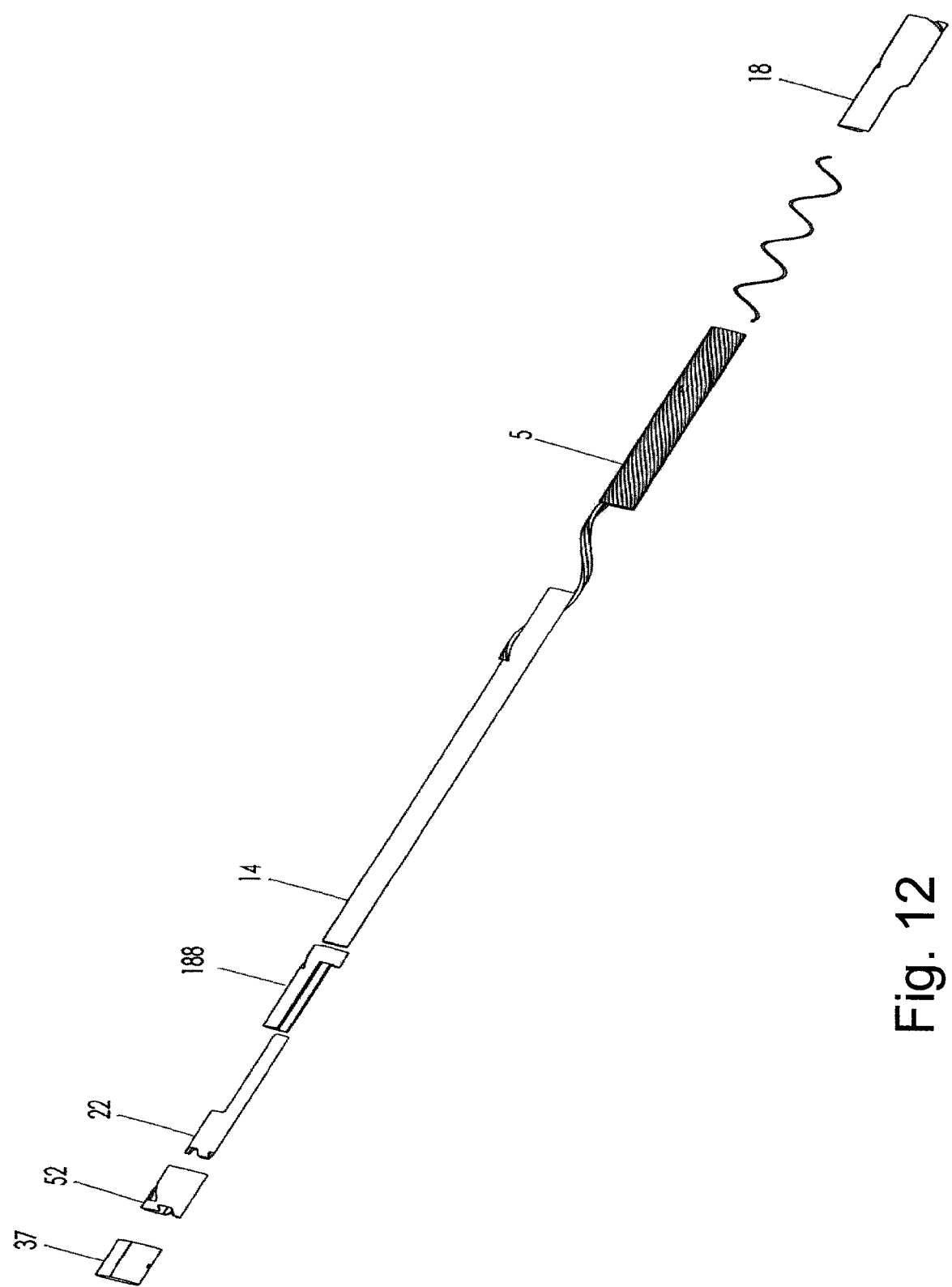
FIG. 12 is an exploded side view of distally located apparatus for enabling concurrent rotation of the inner and outer tubular portions.

FIG. 12 illustrates, in exploded view, distally located apparatus for enabling concurrent rotation of the inner and outer tubular portions. Sleeves 22 and 188, which may be arcuate and may subtend an angle of approximately 160 degrees, are made from the same metallic material, and have identical inner and outer diameters. Sleeve 22 is connected to inner tubular portion 14 and covered by part 52. Sleeve 188 is connected to outer tubular portion 5 and covered by sleeve 18

Since sleeves 22 and 188 have the same diameters and are connected to a corresponding tubular portion, they are in slidable abutting relation with each other. This sliding action enables the inner and outer tubular portions to be linearly displaced one within the other while being concurrently rotatable.

The linear displacement is dependent on the length of the sleeves, corresponding to the change in length needed to expand and contract the helical cutting unit.

In one embodiment, the outer tubular portion is a cable of multi-coil construction arranged such that each coil is tightly wound about the longitudinal axis of the hollow shaft, for example obliquely wound about the longitudinal axis so as to abut with an adjacent coil.

Spiral strands that suitable for the present invention may be made of stainless steel or Nitinol and include the ACTON series of cable tube type FLAT or STD made by Asahi Intecc (Asahi Intecc Co. Ltd., Japan), or the HSS® series of tubes made by Fort Wayne Metals (Fort Wayne, Ind.). The one or more wires or strips that are formed together to define this closely-wound spiral or tube may all have the same diameter, or alternatively, some wires or strips may have a larger diameter than others, thereby forming a coaxial flexible hollow shaft with round or elliptical outer contour and a closely rounded internal lumen. Alternatively, the strands or straps may be made of a plastic material.

Figure 8A:
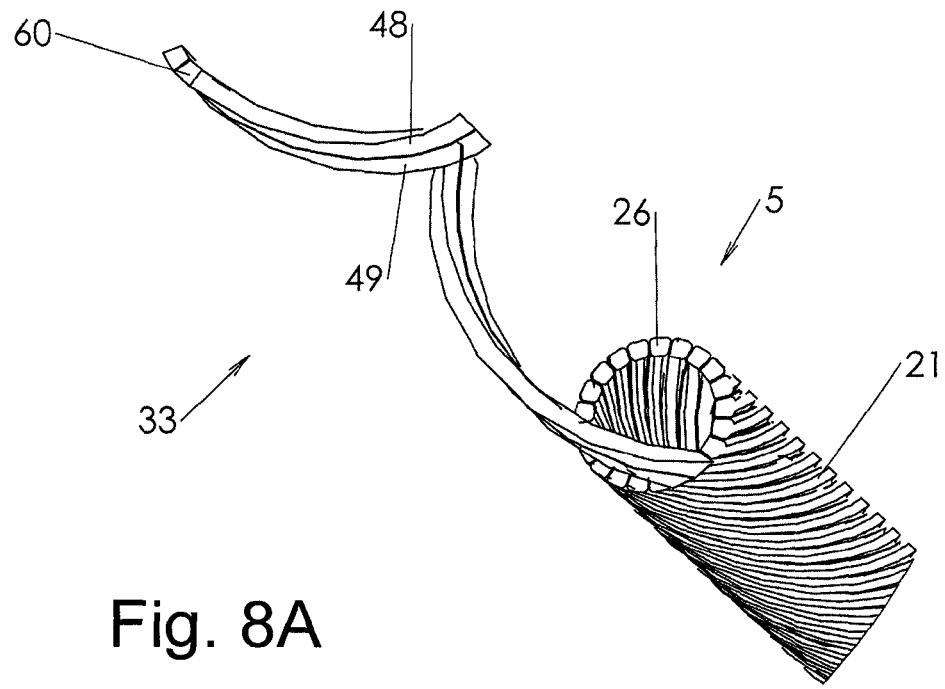
FIG. 8A is a perspective view of an outer tube layer and of a helical cutting unit integrally formed therewith.

As shown in FIG. 8A, helical cutting unit 33 may be integrally formed with outer cable 5 such that the two illustrated joined strands 48 and 49 of helical cutting unit 33 are longer than the other coils 21 of outer cable 5 and distally extend beyond the distal end 26 of outer cable 5. Helical cutting unit 33 may comprise a single strand, or any other desired number of strands.

Nitinol having the characteristic of super elasticity, or Series 300 flexible stainless steel is suitable for the integrally formed and expandable helical cutting unit 33.

With reference to FIGS. 1, 2, 4 and 5, the strands of integrally formed helical cutting unit 33 are radially separated from outer cable 5 by sleeve 18. One portion of cutting unit 33 is fixated within a helical aperture 36 formed in sleeve 18, and its distal end is fixated between metal tube 37 and sleeve 22. The ability to mechanically fixate the strands of helical cutting unit 33 between sleeve 22 and tube 37 obviates the need of having to weld the Nitinol strands of cutting unit 33 to sleeve 22 made of stainless steel. Nitinol and stainless steel are dissimilar metals, so that if welded together, intermetallics are liable to form in a weld zone, resulting in brittle joints. Helical aperture 36 assures that a longitudinally central region of cutting unit 33 will be radially separated by a significantly large and desired distance from outer cable 5, in order to cut the occlusive material by a corresponding diameter, and further urges helical cutting unit 33 to expand at a specific angle and away from outer cable 5.

Alternatively, helical cutting unit 33 is formed separately from outer cable 5, and its two ends are fixated by sleeve 18 and tube 37, respectively.

Figure 9:
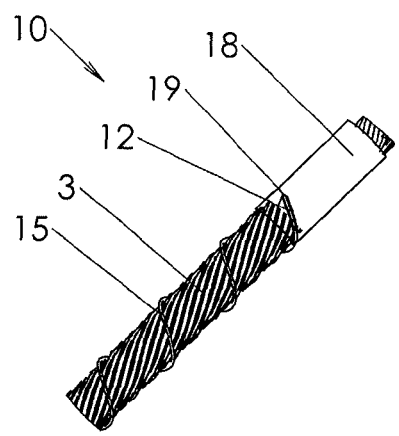
FIG. 9 is a perspective view of an outer cable arrangement for an expandable atherectomy device, according to one embodiment of the present invention.
Figure 10:
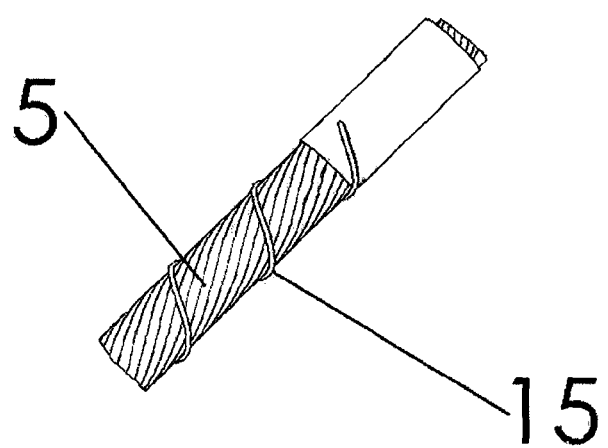
FIG. 10 is a larger scale view of the outer cable arrangement of FIG. 9.

FIGS. 9 and 10 illustrate an outer cable arrangement 10 for an expandable atherectomy device. In order to maintain the adjacent tightly wound spiral strands 3 defining outer cable 5 of the flexible and coaxial hollow shaft in abutting relation with each other and in a uniform shape and diameter, a helical mono-coil spring 15 is wound over outer cable 5. A tubular sleeve 18 is fitted over, and secured such as by welding to, outer cable 5 at each end 12, whether the distal end or proximal end, of mono-coil spring 15, for ensuring suitable mono-coil tension. An aperture 19 for receiving a corresponding mono-coil end 12 is formed in sleeve 18.

Mono-coil spring 15 extends throughout substantially the entire length of outer cable 5, as shown in FIG. 10.

As another means for maintaining the coil uniformity of outer cable 5, helical mono-coil spring 15 has a larger pitch than the pitch of the coils of outer cable 5. The pitch ratio of mono-coil spring 15 to outer cable 5 may range from 1.0-1.1 to 1.0-10. Also, the inner diameter of mono-coil spring 15 is less than or equal to the outer diameter of outer cable 5. Mono-coil spring 15 may be made of any suitable biocompatible material, including stainless steel, memory shape metal, and polymer. The cross section of mono-coil spring 15 may be round, square or any other suitable shape.

In addition to the aforementioned novel structural features, the screw shape of the coils of outer cable 5 or of mono-coil spring 15 help to convey blood and disintegrated atheroma material along the longitudinal axis of the shaft as result of the Archimedes screw effect.

Alternatively or in addition, the adjacent coils of outer cable 5 may be maintained in abutting relation and their expansion may be prevented by applying extra thin-walled heat shrink material, e.g. made of polyester.

Other means for limiting coil expansion include a plurality of longitudinally spaced rings connected to outer cable 5, laser welding and adhesive attachment.

In another embodiment, the helical cutting unit is fixed and inexpandable, and the hollow shaft may be made of a single tubular portion which may be integral with the helical cutting unit. When the helical cutting unit is fixed at a relatively small and fixed radial separation from the hollow shaft, although greater than the other cutting means, the atherectomy device of the present invention is advantageously narrower than prior art atherectomy devices and is therefore capable of removing occlusive material from narrow blood vessels, for example those having a diameter of as small as 2 mm.

Figure 11:
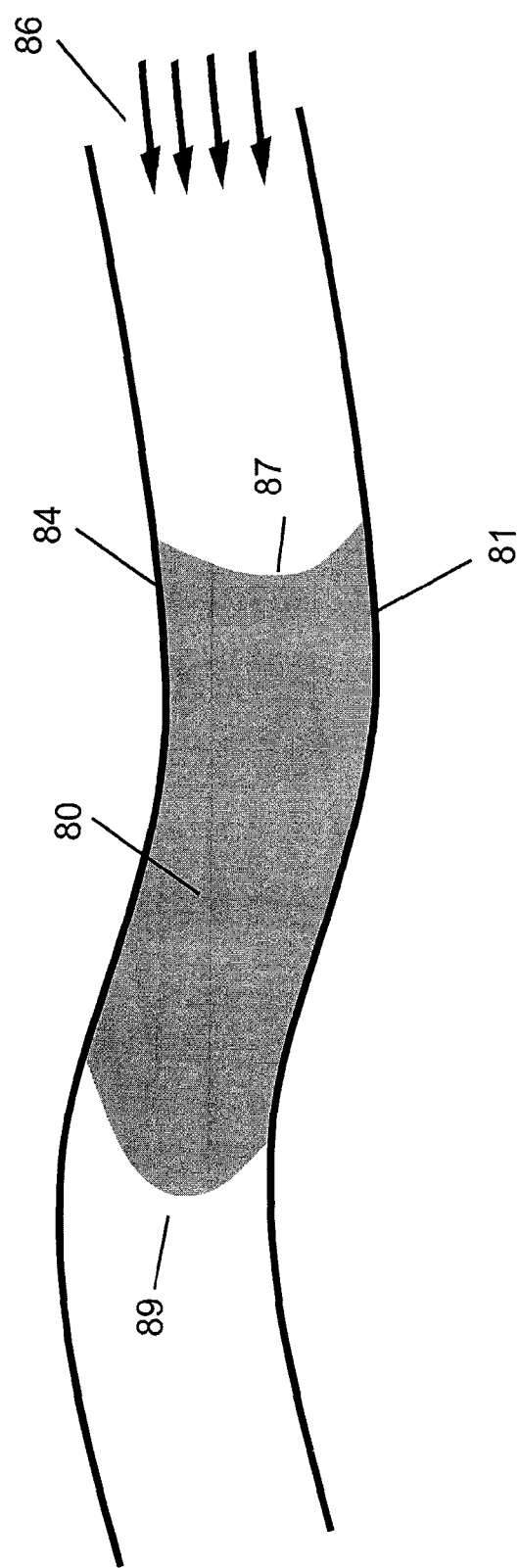
FIG. 11 is a schematic illustration of an occlusion that has formed within a blood vessel.

Prior to describing the unique operation of the atherectomy device, reference is first made to FIG. 11, which schematically illustrates the formation of an occlusion 80 in a blood vessel 81. Occlusion 80 is formed as a result of cardiovascular disease by which fat and cholesterol build up on the walls 84 of blood vessels. As additional occlusive material including plaque forms on the blood vessel walls 84, the lumen of blood vessel 81 becomes narrower and the flowrate of blood therethrough becomes reduced. Eventually the occlusive material accumulates throughout the lumen, and the flow of blow across occlusion 80 ceases.

Due to the pulsating nature of the blood flow 86 in the direction indicated by the arrows that continuously applies a periodic force to the proximal surface 87 of occlusion 80, the proximal surface becomes convex. Also, proximal surface 87 becomes compressed to form hardened plaque and then a CTO, characterized by complete interruption of blood flow. Distal surface 89 of occlusion 89 becomes convex since it is not exposed to pulsating blood flow 86.

The hardness of occlusion 80 is not uniform, containing regions of hard plaques that include calcium and scar tissue and soft plaques that include viscous cholesterol material. The central concave region of proximal surface 87 is always softer that the surrounding regions of proximal surface 87. Soft plaque tends to allow the passage therethrough of a guidewire; however hard plaque deflects a guidewire or a large sized cutting device during an attempt to penetrate occlusion 80. When a prior art cutting device is deflected, the cutting surfaces many times contact and tear blood vessel wall 84.

The use of the atherectomy device of the present device, and particularly of the helical cutting unit, overcomes the aforementioned drawbacks and allows the hard plaque of CTOs to be atraumatically opened and removed.

During the eccentric rotation of the hollow shaft within blood vessel 81, the hollow shaft is caused to be laterally displaced, i.e. displaced in a direction radially spaced from the longitudinal axis of the blood vessel. Eventually the helical cutting unit contacts blood vessel wall 84 as a result of the lateral displacement, and the hollow shaft is consequently caused to be laterally displaced in an opposite direction in response to the impact with blood vessel wall 84. This alternating lateral movement is accompanied by longitudinal displacement initiated by manipulation of the atherectomy device by the physician in order to remove the occlusive material. As a result of the alternating lateral movement, the hollow shaft is substantially self-centered, and the cutting surfaces of the hollow shaft's distal tip are able to pierce a central relatively soft plaque region. The distal tip remains in engagement with relatively soft plaque region after the plaque has been pierced. The other cutting surfaces are then able to enlarge the opening, as described hereinabove.

It will be appreciated that the central relatively soft plaque region pierced by the distal tip during the lateral movement is not necessarily at the true center of the blood vessel.

The self-centering feature based on alternating lateral movement of the atherectomy device is contingent on atraumatic contact between the helical cutting unit and the blood vessel wall. The profile of helical cutting unit 33 shown in FIG. 8A is configured to ensure atraumatic contact between the helical cutting unit and the blood vessel wall during the alternating lateral movement. Each of strands 48 and 49 has a trapezoidal cross section 60 when cut in a plane perpendicular to the longitudinal axis of outer cable 5.

Figure 8B:
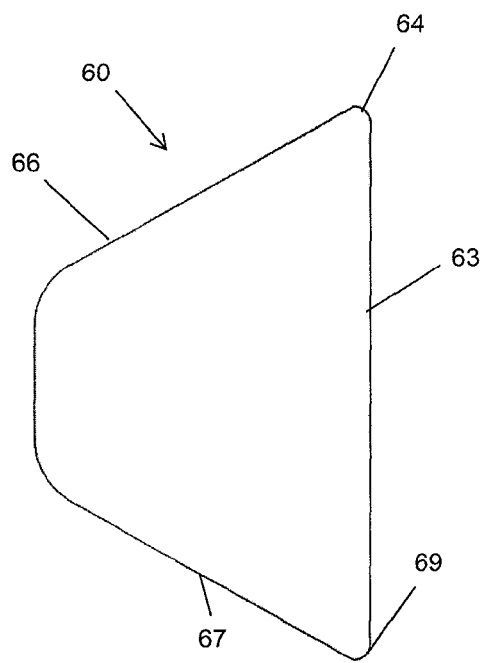
FIG. 8B is a cross sectional view of the cutting unit of FIG. 8A.

As shown in FIG. 8B, a first side 63 of trapezoidal cross section 60, disposed generally laterally outwardly, is adapted to atraumatically contact a wall of the blood vessel during lateral movement of the atherectomy device. A vertex 64 at the intersection of first side 63 and second side 66 adjacent to first side 63 is sufficiently sharp to cut the occlusive material. A vertex 69 at the intersection of first side 63 and third side 67 adjacent to first side 63 and opposite second side 66, however, is dull, being formed with a curved surface having a sufficiently large radius to prevent plaque removal and tearing of the blood vessel wall.

The Applicant has found that a ratio of the length of second side 66 to the length of first side 63 ranging from 1:1.13 is sufficient to prevent vertex 64 from contacting and tearing the blood vessel wall during concurrent eccentric rotation and alternating lateral movement of the hollow shaft. This range is based on a combination of several parameters, including planarity of second side 66, rotation speed of the hollow shaft, motor torque, pushability of the hollow shaft and the relative change in diameter of all the cutting means.

The configuration of trapezoidal cross section 60 is particularly useful for blood vessels having an angular disposition of no greater than 70 degrees, to prevent tearing of the blood vessel wall during navigation through a tortuous blood vessel, although the atherectomy device of the present invention is also applicable to such blood vessels as well.

While prior art atherectomy devices have been unable to penetrate the distal surface of an occlusion in a retrograde approach, and particularly of a CTO, due to its convex formation as shown in FIG. 11, the atherectomy device of the present invention can easily penetrate the distal surface and enlarge the opening, similarly to the method described hereinabove.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:

1. A self-centering atherectomy device configured with a distal portion having a gradually increasing diameter in the proximal direction for opening a chronic total occlusion within a blood vessel being characterized by complete interruption of blood flow, said distal portion comprising:
   a) a rotatably motor-driven flexible hollow shaft that is slidable over, and is coaxial with, a longitudinal axis of a guidewire;
   b) an annular extreme distal tip of the hollow shaft having a first diameter that is only slightly larger than the diameter of the guidewire and configured with circumferentially extending and distally facing cutting surfaces defining said first diameter for piercing hardened atherosclerotic plaque of a chronic total occlusion that has accumulated within a blood vessel;
   c) a tubular sleeve proximally spaced from said extreme distal tip of the hollow shaft, and fitted over, and secured to, a first peripheral surface of the hollow shaft, wherein a distal end of said sleeve has a slightly larger second diameter than said extreme distal tip of the hollow shaft and is configured with cutting surfaces for enlarging an opening formed in the plaque, wherein the cutting surfaces of said sleeve are only distally facing and are not peripheral and diametrically outwardly disposed surfaces; and
   d) an asymmetric and radially rigid cutting unit extending between said sleeve and a second peripheral surface of the hollow shaft which is proximally spaced from said first peripheral surface, said cutting unit defining a diameter larger than said sleeve for additionally enlarging said opening and having a radial separation from said hollow shaft at one longitudinally central region of said cutting unit that is significantly greater than the radial separation from said hollow shaft at other longitudinal regions of said cutting unit,
   wherein all peripheral and diametrically outwardly disposed surfaces of said distal portion are curved to ensure atraumatic contact with a wall of the blood vessel during lateral movement of the atherectomy device,
   wherein the hollow shaft, in cooperation with the significant radially separated configuration at said one central region of said cutting unit and with operation of a motor, is eccentrically rotatable about the longitudinal axis to result in lateral displacement in a first direction within the blood vessel and subsequently in a second direction opposite to said first direction in response to atraumatic impact between said cutting unit and a wall of the blood vessel, so as to be substantially self-centered within the blood vessel as a result of alternating lateral movement,
   wherein the cutting surfaces of said extreme distal tip, during distal displacement of the atherectomy device and following a self-centering action, are configured to pierce a central relatively soft plaque region of the chronic total occlusion, and the cutting surfaces of said sleeve and of said cutting unit are configured to sequentially enlarge the opening while said extreme distal tip remains in engagement with said central region.

2. The atherectomy device according to claim 1, wherein the cutting unit is a radially rigid helical strand unit that radially protrudes from the sleeve and from the second peripheral surface of the hollow shaft, said helical strand unit being wound about the hollow shaft in such a way that only one diametrical end of the hollow shaft is surrounded by said helical strand unit for a given axial length of the hollow shaft.

3. The atherectomy device according to claim 2, wherein the helical strand unit is a helical strand drilling unit that is configured with a trapezoidal cross section having a laterally outwardly disposed side, a laterally inwardly disposed side defining a diameter larger than the cutting surfaces of the extreme distal tip and which is significantly shorter than said laterally outwardly disposed side, and two opposite intermediate sides each extending between a corresponding end of said laterally inwardly disposed side and said laterally outwardly disposed side.

4. The atherectomy device according to claim 2, wherein the hollow shaft comprises coaxial inner and outer tube layers to each of which a corresponding end of the helical strand unit is secured or attached, and an actuator which is operable to cause longitudinal displacement of one of said inner and outer tube layers relative to the other and to induce selective expansion of the helical strand unit.

5. The atherectomy device according to claim 4, wherein the outer tube layer is a cable of multi-coil construction.

6. The atherectomy device according to claim 5, further comprising a coil expansion limiter secured or attached to the outer tube layer, for increasing compressive strength of the outer tube layer.

7. The atherectomy device according to claim 6, wherein the coil expansion limiter is a helical mono-coil spring wound over the cable of the outer tube layer and having a larger pitch than the pitch of the coils of the outer tube layer, to maintain a substantially uniform outer cable shape and diameter.

8. The atherectomy device according to claim 7, wherein a pitch ratio of the cable of the outer tube layer to the mono-coil spring ranges from 1.0-1.1 to 1.0-10.

9. The atherectomy device according to claim 7, further comprising an additional tubular sleeve fitted over, and secured to the cable of the outer tube layer at the second peripheral surface of the hollow shaft, a first aperture being formed in said additional sleeve by which the one central region of the helical strand unit which has the significant radially separated configuration is fixated and a second aperture for receiving a corresponding end of the mono-coil spring being formed in said additional sleeve.

10. The atherectomy device according to claim 9, wherein the additional tubular sleeve is secured to the outer tube layer by means of a further sleeve connected to the outer tube layer and covered by the additional tubular sleeve, said further sleeve being of a same diameter as the sleeve secured to the first peripheral surface of the hollow shaft, wherein the sleeve secured to the first peripheral surface of the hollow shaft which is connected to the inner tube layer, to allow the sleeve secured to the first peripheral surface of the hollow shaft and the further sleeve to be in abutting relation with each other while rotating concurrently.

11. The atherectomy device according to claim 7, wherein the outer tube layer and the inner tube layer are in abutting relation with each other at both proximal and distal portions thereof while rotating concurrently.

12. The atherectomy device according to claim 4, wherein the actuator is configured with a proximal port in communication with a lumen of the hollow shaft, through which contrast material is injectable.

13. The atherectomy device according to claim 12, wherein the inner tube layer is made of liquid impervious material or is applied with liquid impervious material.

14. The atherectomy device according to claim 4, wherein the sleeve is connected to the outer tube layer, for ensuring coaxial and concurrent rotation of the inner and outer tube layers substantially throughout the entire length of the hollow shaft.

15. The atherectomy device according to claim 2, further comprising a metal tube surrounding and engaged with the sleeve, wherein a distal end of the helical strand unit is secured between said metal tube and said sleeve.

16. The atherectomy device according to claim 15, wherein a distal end of the metal tube is formed with one or more cutting surfaces for further enlarging the opening formed in the plaque.

17. The atherectomy device according to claim 15, wherein the helical strand unit is made of Nitinol and the sleeve is made of stainless steel.

18. The atherectomy device according to claim 1, wherein the cutting unit is connected or secured to the sleeve and to the second peripheral surface of the hollow shaft.

19. The atherectomy device according to claim 1, which is usable to penetrate a distal surface of a chronic total occlusion in a retrograde approach.

20. A laterally self-directed atherectomy device for locating and piercing a relatively soft plaque region of a chronic total occlusion within a blood vessel which is characterized by complete interruption of blood flow and formation of hardened atherosclerotic plaque, and for enlarging a pierced opening within the chronic total occlusion, said atherectomy device comprising a distal portion which is unrestrained by a guidewire when the relatively soft plaque region is pierced, wherein said distal portion comprises:
  a) a rotatably motor-driven flexible hollow shaft;
  b) an annular extreme distal tip of the hollow shaft configured with circumferentially extending and distally facing cutting surfaces for piercing a relatively soft plaque region of a chronic total occlusion that has accumulated within a blood vessel; and
  c) an asymmetric and radially rigid helical strand drilling unit connected to the hollow shaft for enlarging a pierced opening formed by the cutting surfaces of the extreme distal tip, the helical strand drilling unit configured with a drilling inducing trapezoidal cross section having a laterally outwardly disposed side, a laterally inwardly disposed side defining a diameter larger than the cutting surfaces of the extreme distal tip and which is significantly shorter than said laterally outwardly disposed side, and two opposite intermediate sides each extending between a corresponding end of said laterally inwardly disposed side and said laterally outwardly disposed side,
wherein the helical strand drilling unit is wound about the hollow shaft in such a way that only one diametrical end of the hollow shaft is surrounded by the helical strand drilling unit for a given longitudinal length of the hollow shaft, and has a radial separation from the hollow shaft at one longitudinally central region of the helical strand drilling unit that is significantly greater than the radial separation from the hollow shaft at other longitudinal regions of the helical strand drilling unit, to facilitate eccentric rotation of the hollow shaft about a longitudinal axis of the atherectomy device for cutting and removing occlusive material from the blood vessel,
wherein all peripheral and diametrically outwardly disposed surfaces of said distal portion are curved to ensure atraumatic contact with a wall of the blood vessel during lateral movement of the atherectomy device,
wherein the hollow shaft, in cooperation with the significant radially separated configuration at said one central region of said helical strand drilling unit and with operation of a motor, is eccentrically rotatable about the longitudinal axis to result in lateral displacement in a first direction within the blood vessel and subsequently in a second direction opposite to said first direction in response to atraumatic impact between the helical strand drilling unit and a wall of the blood vessel,
wherein the cutting surfaces of the extreme distal tip, during distal displacement of the atherectomy device and following the lateral displacement, are deflected upon contact with a hardened plaque region of the chronic total occlusion and are configured, upon contact with the relatively soft plaque region of the chronic total occlusion, to pierce the relatively soft plaque region, and leading intermediate side surfaces of the helical strand drilling unit with respect to a rotational direction of the hollow shaft are configured to sequentially enlarge the pierced opening during a drilling operation while said extreme distal tip remains in engagement with the relatively soft plaque region.

21. A self-centering atherectomy device configured with a distal portion having a gradually increasing diameter in the proximal direction for opening a chronic total occlusion within a blood vessel being characterized by complete interruption of blood flow, said distal portion comprising:
   a) a rotatably motor-driven flexible hollow shaft that is slidable over, and is coaxial with, a longitudinal axis of a guidewire;
   b) an annular extreme distal tip of the hollow shaft having a first diameter that is only slightly larger than the diameter of the guidewire and configured with circumferentially extending and distally facing cutting surfaces defining said first diameter for piercing hardened atherosclerotic plaque of a chronic total occlusion that has accumulated within a blood vessel;
   c) a tubular sleeve proximally spaced from said extreme distal tip of the hollow shaft, and fitted over, and secured to, a first peripheral surface of the hollow shaft, wherein a distal end of said sleeve has a slightly larger second diameter than said extreme distal tip of the hollow shaft and is configured with cutting surfaces for enlarging an opening formed in the plaque; and
   d) an asymmetric cutting unit extending between said sleeve and a second peripheral surface of the hollow shaft which is proximally spaced from said first peripheral surface, said cutting unit defining a diameter larger than said sleeve for additionally enlarging said opening and having a radial separation from said hollow shaft at one longitudinally central region of said cutting unit that is significantly greater than the radial separation from said hollow shaft at other longitudinal regions of said cutting unit, wherein said cutting unit is inexpandable and is integral with the hollow shaft, wherein all peripheral and diametrically outwardly disposed surfaces of said distal portion are curved to ensure atraumatic contact with a wall of the blood vessel during lateral movement of the atherectomy device, wherein the hollow shaft, in cooperation with the significant radially separated configuration at said one central region of said cutting unit and with operation of a motor, is eccentrically rotatable about the longitudinal axis to result in lateral displacement in a first direction within the blood vessel and subsequently in a second direction opposite to said first direction in response to atraumatic impact between said cutting unit and a wall of the blood vessel, so as to be substantially self-centered within the blood vessel as a result of alternating lateral movement, wherein the cutting surfaces of said extreme distal tip, during distal displacement of the atherectomy device and following a self-centering action, are configured to pierce a central relatively soft plaque region of the chronic total occlusion, and the cutting surfaces of said sleeve and of said cutting unit are configured to sequentially enlarge the opening while said extreme distal tip remains in engagement with said central region.

* * * * *

UNITED STATES PATENT AND TRADEMARK OFFICE
CERTIFICATE OF CORRECTION

PATENT NO.        : 10,702,299 B2
APPLICATION NO.   : 15/323410
DATED             : July 7, 2020
INVENTOR(S)       : Swi Barak et al.

It is certified that error appears in the above-identified patent and that said Letters Patent is hereby corrected as shown below:

In the Claims

Column 13, Claim 10, Line 31, after "shaft" delete "which".

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*